(12) United States Patent
Wang et al.

(10) Patent No.: US 12,396,625 B2
(45) Date of Patent: Aug. 26, 2025

(54) ULTRA-COMPACT MICROSYSTEMS-BASED SINGLE AXIS CONFOCAL ENDOMICROSCOPE

(71) Applicant: THE REGENTS OF THE UNIVERSITY OF MICHIGAN, Ann Arbor, MI (US)

(72) Inventors: Thomas D. Wang, Ann Arbor, MI (US); Xiyu Duan, San Jose, CA (US); Gaoming Li, Ann Arbor, MI (US); Haijun Li, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 884 days.

(21) Appl. No.: 17/439,722

(22) PCT Filed: Mar. 18, 2020

(86) PCT No.: PCT/US2020/023405
§ 371 (c)(1),
(2) Date: Sep. 15, 2021

(87) PCT Pub. No.: WO2020/191083
PCT Pub. Date: Sep. 24, 2020

(65) Prior Publication Data
US 2022/0160232 A1 May 26, 2022

Related U.S. Application Data

(60) Provisional application No. 62/820,256, filed on Mar. 18, 2019.

(51) Int. Cl.
*A61B 5/00* (2006.01)
*A61B 1/00* (2006.01)
(Continued)

(52) U.S. Cl.
CPC .... *A61B 1/00172* (2013.01); *A61B 1/000095* (2022.02); *A61B 5/0068* (2013.01);
(Continued)

(58) Field of Classification Search
CPC .......... A61B 1/00172; A61B 1/000095; A61B 5/0068; G02B 21/0028; G02B 21/0032; G02B 21/0048
(Continued)

(56) References Cited

U.S. PATENT DOCUMENTS

| 5,059,009 A | 10/1991 | McKinley |
| 6,545,260 B1 | 4/2003 | Katashiro et al. |

(Continued)

FOREIGN PATENT DOCUMENTS

| WO | WO-2018/102822 A1 | 6/2018 |
| WO | WO-2019/023287 A1 | 1/2019 |

OTHER PUBLICATIONS

European Patent Application No. 20773102.7, Extended European Search Report, dated Sep. 1, 2022.
(Continued)

*Primary Examiner* — Wyatt A Stoffa
*Assistant Examiner* — Grant A Gagnon
(74) *Attorney, Agent, or Firm* — MARSHALL, GERSTEIN & BORUN LLP

(57) ABSTRACT

A compact single-axis confocal endomicroscope is provided, capable of complying within 2.8 mm diameter endoscope space requirements. The single-axis confocal endomicroscope uses a folded path design achieved between a fixed mirror and a lateral plane scanning mirror thereby producing a high numerical aperture that allows for diffraction-limited resolution with sub-surface depths. The scanning mirror is formed on a fixed-position, scanning MEMS assembly and has a central aperture that allows for illumi-
(Continued)

nation beam expansion in the folded path design. A series of spacers are used to retain beam focusing optical elements in fixed positioned relative to the scanning MEMS assembly for coupling with a single mode fiber.

9 Claims, 20 Drawing Sheets

(51) Int. Cl.
    *A61B 1/07*         (2006.01)
    *G02B 21/00*       (2006.01)

(52) U.S. Cl.
    CPC ..... *G02B 21/0028* (2013.01); *G02B 21/0032* (2013.01); *G02B 21/0048* (2013.01)

(58) Field of Classification Search
    USPC ....................................................... 359/368
    See application file for complete search history.

(56) References Cited

U.S. PATENT DOCUMENTS

| | | |
|---|---|---|
| 2009/0028407 A1 | 1/2009 | Seibel et al. |
| 2011/0211104 A1 | 9/2011 | Hendriks |
| 2012/0075685 A1 | 3/2012 | Hofmann et al. |
| 2016/0357008 A1 | 12/2016 | Li et al. |
| 2018/0356629 A1 | 12/2018 | Wang et al. |

OTHER PUBLICATIONS

Deliolanis et al., Performance of the red-shifted fluorescent proteins in deep-tissue molecular imaging applications, J. Biomed. Opt., 13(4):044008 (2008).
Duan et al., MEMS-based multiphoton endomicroscope for repetitive imaging of mouse colon, Biomedical Optics Express, vol. 6, No. 8, 10 pp. (Aug. 2015).
Duan et al., Visualizing epithelial expression of EGFR in vivo with distal scanning side-viewing confocal endomicroscope, Sci. Rep., 6:37315 (2016).
Duan, MEMS-Based Confocal Endomicroscope for High Resolution Fluorescence Imaging, Dissertation, University of Michigan, 2017.
Hinoi et al., Mouse model of colonic adenoma-carcinoma progression based on somatic Apc inactivation, Cancer Res., 67(20):9721-30 (2007).
Hinoi et al., Silencing of CDX2 expression in colon cancer via a dominant repression pathway, J. Biol. Chem., 278(45):44608-16 (2003).
International Application No. PCT/US2020/023405, International Preliminary Report on Patentability, dated Sep. 16, 2021.
International Application No. PCT/US2020/023405, International Search Report and Written Opinion, mailed Jun. 10, 2020.
Kang et al., Endoscopic probe optics for spectrally encoded confocal microscopy, Biomed. Opt. Express, 4(10):1925-36 (2013).
Kim et al., In vivo wide-area cellular imaging by side-view endomicroscopy, Nat. Methods, 7(4):303-5 (2010).
Li et al., Integrated monolithic 3D MEMS scanner for switchable real time vertical/horizontal cross-sectional imaging, Opt. Express, 24(3):2145-55 (2016).
Li et al., Ultra-compact microsystems-based single axis confocal endomicroscope, IEEE Transactions on Medical Imaging, vol. 39, Issue 7, pp. 2406-2414 (Jul. 2020).
Lopez-Garcia et al., Intestinal stem cell replacement follows a pattern of neutral drift, Science, 330(6005):822-5 (2010).
Madisen et al., A robust and high-throughput Cre reporting and characterization system for the whole mouse brain, Nat. neurosci., 13(1):133-40 (2010).
Marten et al., Detection of dysplastic intestinal adenomas using enzyme-sensing molecular beacons in mice, Gastroenterology, 12292):406-14 (2002).
Rakic, Algorithm for the determination of intrinsic optical constants of metal films: application to aluminum, Appl. Opt., 34(22):4755-67 (1995).
Rowan et al., APC mutations in sporadic colorectal tumors: A mutational "hotspot" and interdependence of the "two hits", Proc. Natl. Acad. Sci. USA, 97(7):3352-7 (2000).
Skala et al., In vivo multiphoton microscopy of NADH and FAD redox states, fluorescence lifetimes, and cellular morphology in precancerous epithelia, Proc. Natl. Acad. Sci. USA, 104(49):19494-9 (2007).
Turner et al., Five parametric resonances in a microelectromechanical system, Nature, 396:149-52 (1998).
Wang et al., Functional imaging of colonic mucosa with a fibered confocal microscope for real-time in vivo pathology, Clin. Gastroenterol. Hepatol., 5(11):1300-5 (2007).
Wang et al., Gradient index lens based combined two-photon microscopy and optical coherence tomography, Opt. Express, 22(11):12962-70 (2014).
Zhou et al., EGFR Overexpressed in Colonic Neoplasia Can be Detected on Wide-Field Endoscopic Imaging, Clin. Transl. Gastroenterol., 6(7):e101 (2015).

ULTRA-COMPACT MICROSYSTEMS-BASED SINGLE AXIS CONFOCAL ENDOMICROSCOPE

CROSS REFERENCE TO RELATED APPLICATIONS

This application claims priority to U.S. Provisional Patent Application No. 62/820,256 filed Mar. 18, 2019, which is hereby incorporated by reference in its entirety.

STATEMENT OF GOVERNMENT SUPPORT

This invention was made with government support under CA142750 awarded by the National Institutes of Health. The government has certain rights in the invention.

FIELD OF THE DISCLOSURE

The present disclosure generally relates to techniques for imaging tissue using an optical instrument and, more particularly, to techniques using ultra-compact single-axis confocal configuration endomicroscopes.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Medical endoscopes have been developed to perform wide-field imaging of the epithelium in hollow organs throughout the human body, in vivo, using white light illumination. In other examples, endoscopes have been used to produce fluorescence imaging remotely by delivering light through a flexible optical fiber.

Endoscopes are evolving toward a thinner overall diameter, and most are equipped with an instrument channel that is 2.8 mm in dimension. Instruments that can pass forward through this channel can have broad clinical applications. A large bending angle at the channel entrance requires the dimensions of the rigid tip to be less than 2.4 mm in diameter with a length less than 10 mm. This small size requirement poses a significant challenge for packaging and alignment.

Confocal microscopes are an example type of endoscope used in medical imaging applications to examine tissue at a particular depth or plane of focus. Confocal microscopes commonly use a pinhole to collect only light that originates from the plane of focus while rejecting light scattered by tissue. Confocal laser endomicroscopy (CLE) is an example endoscopic technique that uses the core of an optical fiber as the pinhole. CLE's have been developed for real time, in vivo, imaging, with some success.

CLE techniques have been used in clinical settings to visualize live tissue with sub-cellular resolution. These techniques, for example, have been used in clinical settings to instantaneously collect "optical biopsies" in vivo. Ideally, these techniques could provide physicians with rapid histological assessment at the point-of-care, minimizing the number and hence cost of physical tissue biopsies. Over diagnosis may be reduced and diagnostic yield may improve. Furthermore, procedural risks, such as bleeding, infection, and perforation, may be reduced.

Yet, despite the promise of CLE techniques, current designs are limited. There is a need for MEMS-based CLE systems capable of for real-time in vivo imaging using compact 2.8 mm or below instrument form factor.

SUMMARY

The present application describes single-axis confocal endomicroscopes, in a compact design, that may be used for imaging of tissue, in vivo. The techniques may be used to provide handheld optical devices for real-time tissue scanning and 3D optical imaging for "optical biopsy" and other applications.

In some examples, the present techniques include microsystems-based confocal laser endomicroscopy (CLE) devices that use a folded optical path to achieve a high numerical aperture (NA) in an ultra-compact package. In some examples, a distal tip end of these devices may be scaled down in dimensions to provide easy forward passage through a 2.8 mm instrument channel of a standard medical endoscope, thereby allowing for broad clinical use by community physicians.

In accordance with an example, an endomicroscope assembly comprises: a flexible tubing having a ferrule and single-mode optical fiber extending into the ferrule, the flexible tubing having a distal end positioned to emit an illumination beam provided when provided to the single-mode optical fiber; a compact scanning assembly mounted to the flexible tubing, the compact scanning assembly having a folded beam configuration to receive the illumination beam, to convert the illumination beam to a higher numerical aperture illumination beam, and to scan the higher numerical aperture illumination beam across a lateral sample region, the compact scanning assembly comprising: a rigid outer housing; a lateral scanning assembly fixedly positioned within the rigid outer housing and adjacent the distal end of the flexible tubing, the lateral scanning assembly having a scanning mirror with an aperture aligned with the single mode fiber to receive the illumination beam into a folded beam path for converting to the higher numerical aperture illumination beam, the folded beam path being defined by the scanning mirror and a fixed mirror, the later scanning assembly having a comb filter drive for scanning the scanning mirror; a lens assembly fixedly positioned within the rigid outer housing, the lens assembly positioned distally to the lateral scanning assembly to scan the higher numerical aperture illumination beam across the later sample region; and a spacer fixedly positioned within the rigid outer housing and distally to the lateral scanning assembly, the spacer having spring members that fixedly suspend the fixed mirror.

BRIEF DESCRIPTION OF THE DRAWINGS

For a more complete understanding of the disclosure, reference should be made to the following detailed description and accompanying drawing figures, in which like reference numerals identify like elements in the figures, and in which.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an optical instrument has an actuator mechanism that generates a high image resolution through an optical instrument that can quickly scan deep into a tissue to create volumetric images. The optical components of the instrument may be sized small enough to easily move about and be manipulated in desired tissue. By using piezoelectric actuation, low-profile scanning devices can achieve large, high-speed displacement of optical components (e.g., mirrors) via microactuation, which allows for real-time cross-sectional and/or 3D images of tissue.

Figure 1:
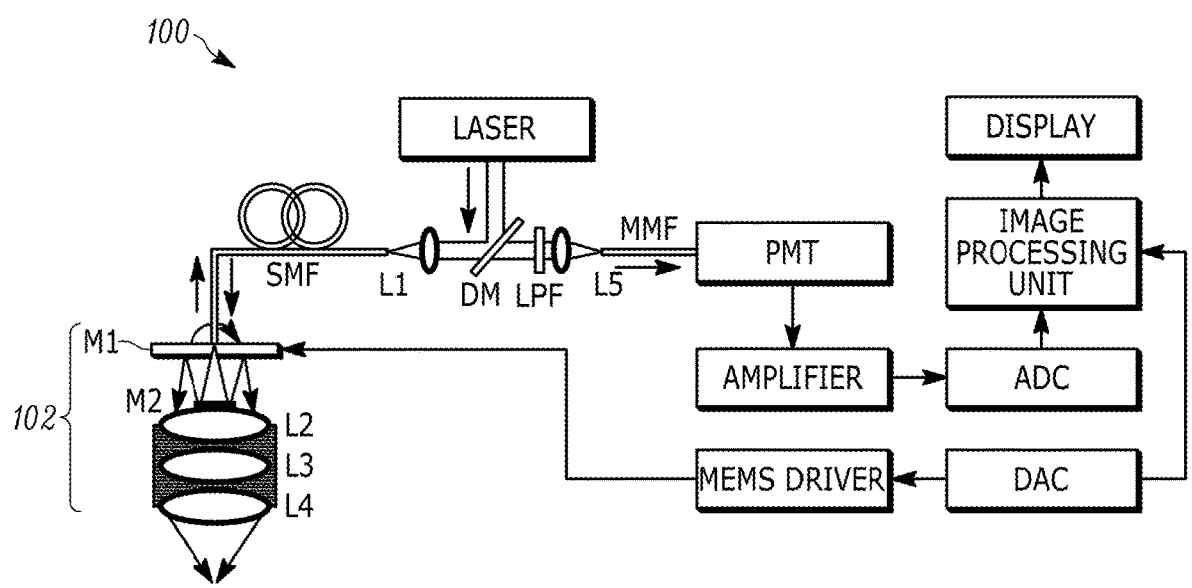
FIG. 1 illustrates a schematic of an endomicroscope imaging system having a single-axis confocal endomicroscope, in accordance with an example.

FIG. 1 illustrates a schematic 100 of an optical imaging system. The system 100 includes a single-axis confocal endomicroscope 102 for performing optical scanning on a sample. The optical scanning may be performed on an outer surface of a tissue sample. However, in examples detailed herein regarding FIG. 1, the endomicroscope scans at a sub-surface focal plane in the tissue, thereby allowing sub-surface in vivo scanning, including optical biopsy scanning.

In the illustrated example, the single-axis confocal endomicroscope 102 is coupled to a single mode fiber (SMF). The SMF is coupled to receive an illumination beam (also termed an excitation beam) provided from a laser source configured to provide that illumination beam via a dichroic mirror (DM) and a focusing element L1 focusing the illumination beam into the SMF. The illumination beam is focused to a focal plane subsurface in the tissue by the single-axis confocal endomicroscope 102, and that illumination beam may be scanned over that focal plane as described further.

A collected fluorescence reflected from that focal plane is collected by the single-axis confocal endomicroscope 102 and provided to a photomultiplier (PMT) through the first focusing element L1, the DM, an optical long pass edge filter (LPF), a second focusing element L5, and multi-mode fiber (MMF). The collected fluorescence from the PMT is provided to an amplifier coupled to an analog-to-digital converter (ADC), which is coupled to an image processing unit. The image processing unit analyzes the collected fluorescence and processes the collected fluorescence beam to produce an output image provided to medical professions on a display. In some examples, the image processing unit may be part of a diagnostic system, where the image processing unit analyzes the collected fluorescence to identify pathologies and pathology locations in the image data. In some examples, the image processing unit may be part of a treatment system, where the image processing unit develops a treatment response based on that identify pathology information.

In the illustrated example, the image processing unit also controls operation of the single-axis confocal endomicroscope 102. The image processing unit is coupled to a digital-to-analog converter (DAC) and generates scanning control sends which are sent to the DAC, which sends those scanning control signals to a MEMS driver of the endomicroscope 102. The scanning control signals control scanning operations of the single-axis confocal endomicroscope 102. For example, the MEMS driver may control scanning of the single-axis confocal endomicroscope 102 by controlling scanning of a mirror, M1, discussed further below.

In operation, according to an example, a fluorescence excitation (also termed an illumination beam) is provided at a wavelength of $\lambda_{ex}$=488 nm. The illumination beam reflects off the DM, and is focused by L1 into the SMF. The illumination beam at the distal end of the SMF passes through a center aperture in the scan mirror M1, reflects off the fixed mirror M2, and is scanned laterally in the tissue sample. For example, the illumination beam is scanned along a X-axis and a Y-axis, defining a lateral scanning plane. This illumination beam scanning may be performed by a MEMS driver controlling scanning of the mirror M1 through lens (L2, L3, and L4). Fluorescence from the tissue sample is collected by the same optics (i.e., lenses L4, L3, and L2), descanned by M1, and focused back into the SMF as a fluorescence beam. The fluorescence beam passes through the DM and the LPF (such as a 488 nm edge LPF), is focused by lens L5 into the MMF. The fluorescence beam is detected by the PMT. The signal is amplified and digitized via the ADC and is reconstructed in the image processing unit.

Figure 2A:
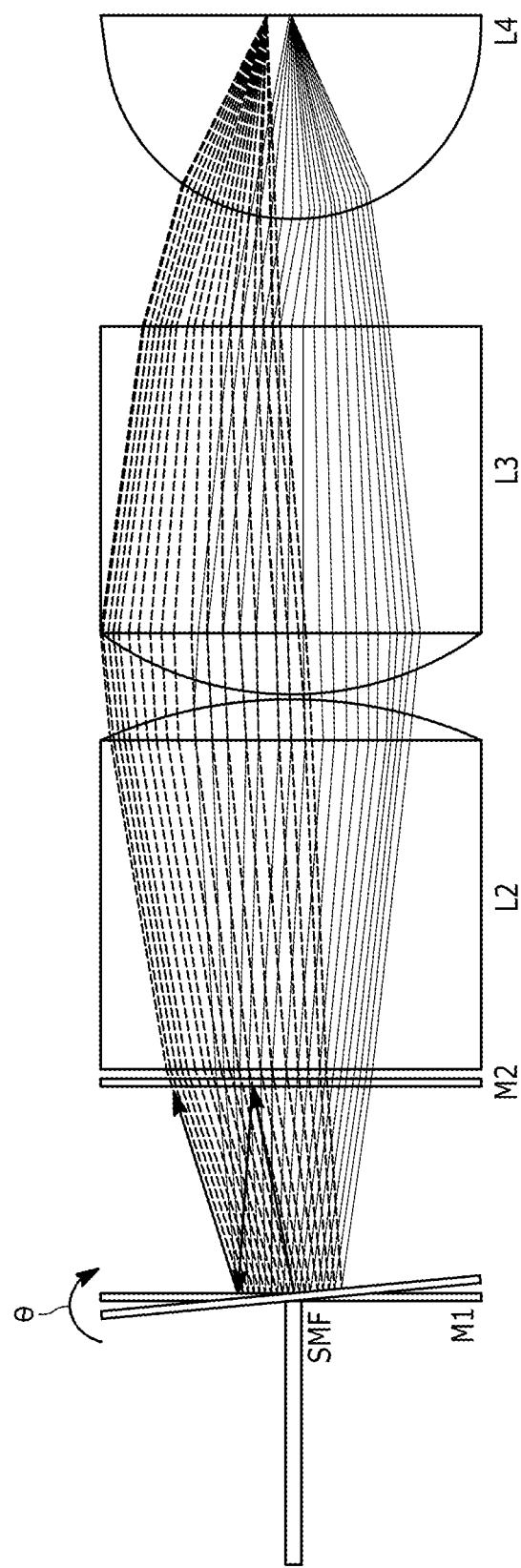
FIGS. 2A-2G illustrates a simulation of optical characteristics of an example implementation of the single-axis confocal endomicroscope of FIG. 1, in accordance with an example.
Figure 2B:
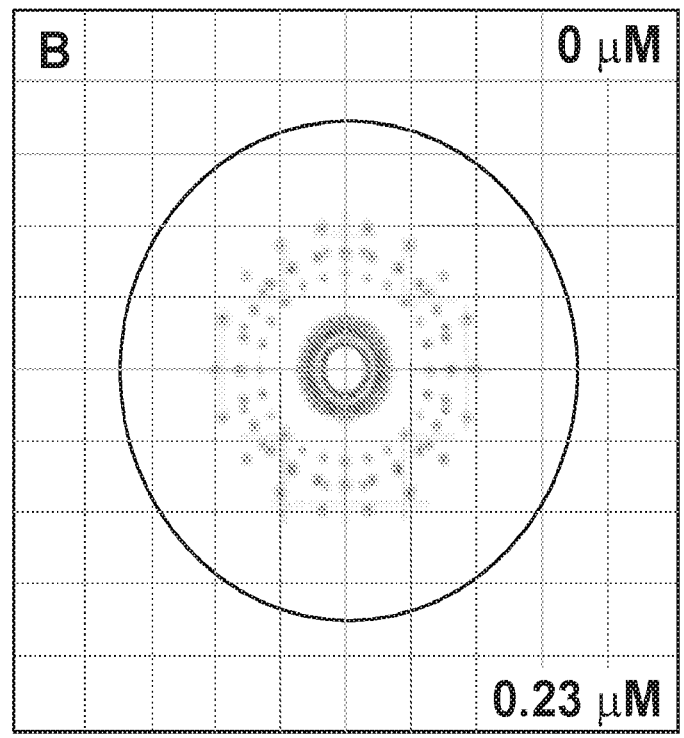
Figure 2C:
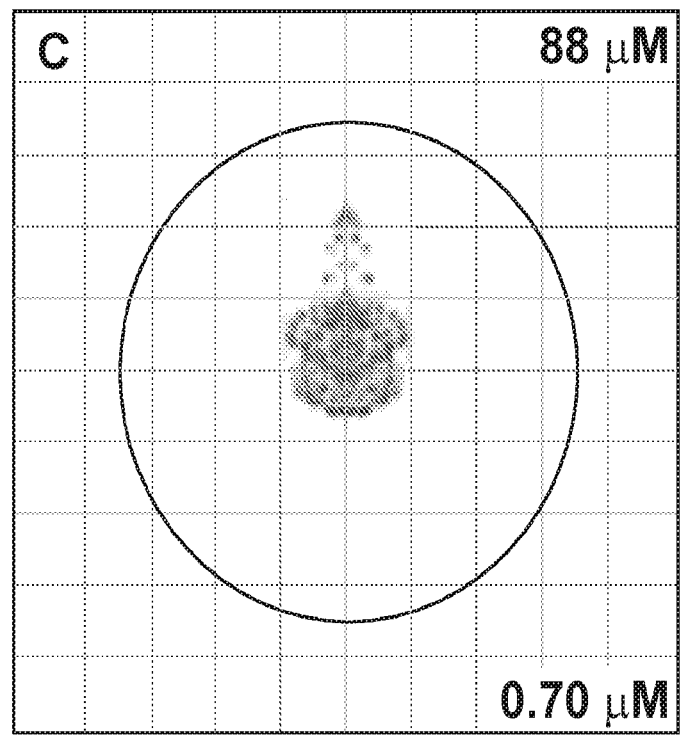
Figure 2D:
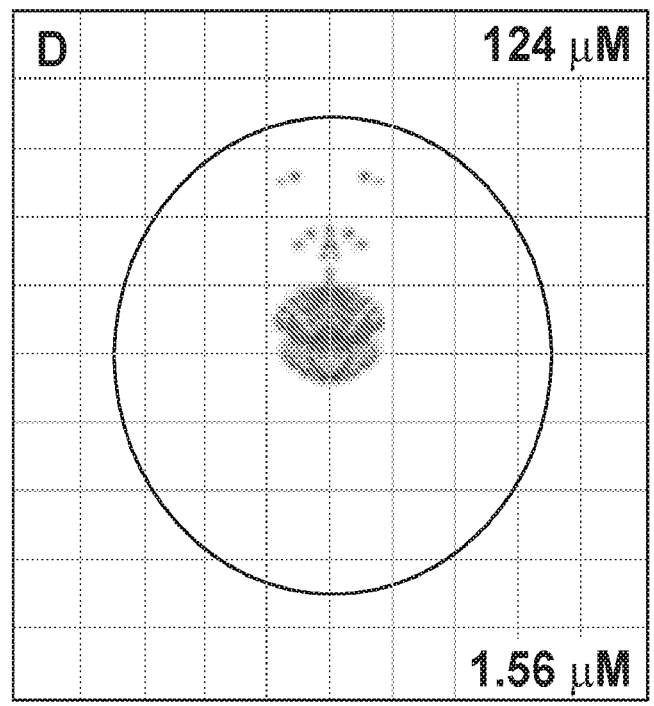
Figure 2E:
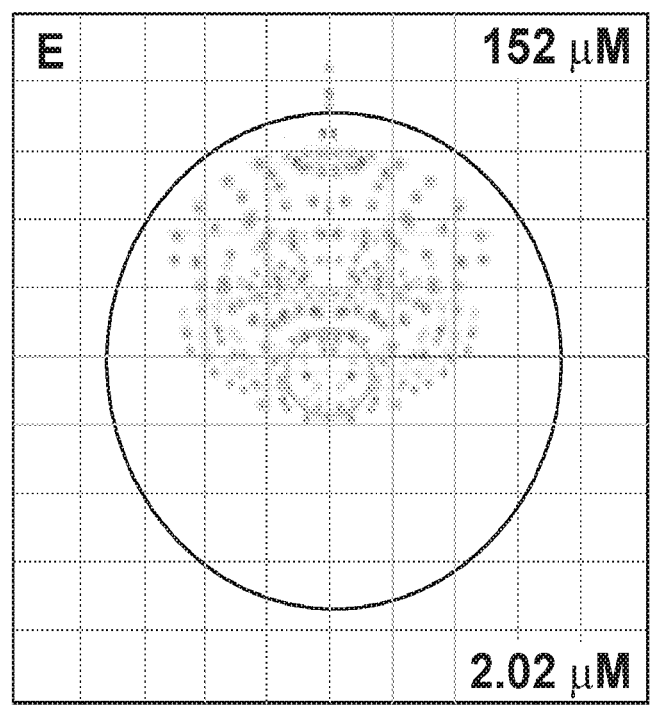
Figure 2F:
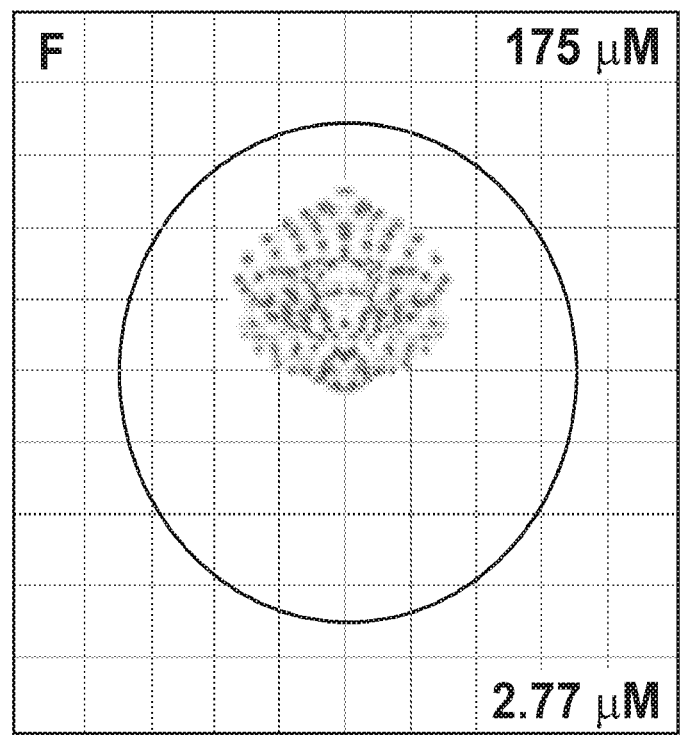
Figure 2G:
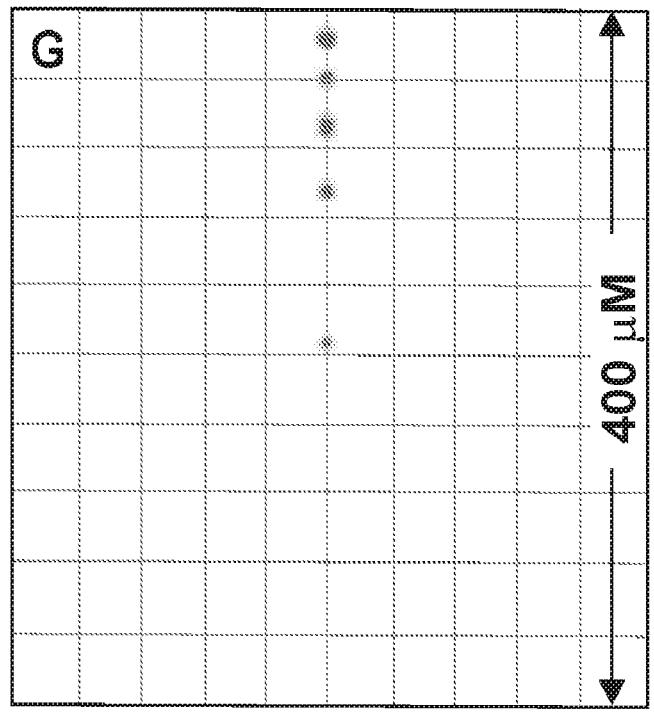

FIG. 2A illustrates an example beam propagation through lenses of the endomicroscope 102, including the scanning operation of mirror M1. The illumination beam exists the SMF and passes through a central aperture in mirror M1 and hits fixed mirror M2. The illumination beam expands as it reflects off the fixed mirror M1 and back to mirror M1 for scanning, where M1 scans about a scanning angle, θ. The illumination beam reflected from scanning mirror M1 is focused by achromat lenses L2 (65568, Edmund Optics) and L3 (65567, Edmund Optics) and then by a plano convex lens L4 (90858, Edmund Optics), resulting in an overall NA=0.41. In the illustrated example, the optical system is diffraction limited with a spot size <0.71 μm up to 150 μm from the image center, as shown in FIGS. 2B-2F. Spot sizes (RMS radius) of 0.23 μm, 0.7 μm, 1.56 μm, 2.02 μm, and 2.77 μm can be achieved at a distance of 0, 88, 124, 152, and 175 μm away from the center, as shown in FIGS. 2B-2F, respectively. The chromatic focus shifts <1.42 μm in the Z-axis over a wavelength range of 480-600 nm for compatibility with a broad range of excitation wavelengths. By way of example, in the illustrated example, a field of review (FOV) of 350×350 μm$^2$ was created when M1 deflected at a mechanical scan angle of 0=±8.25 deg, FIG. 2G.

Figure 3:
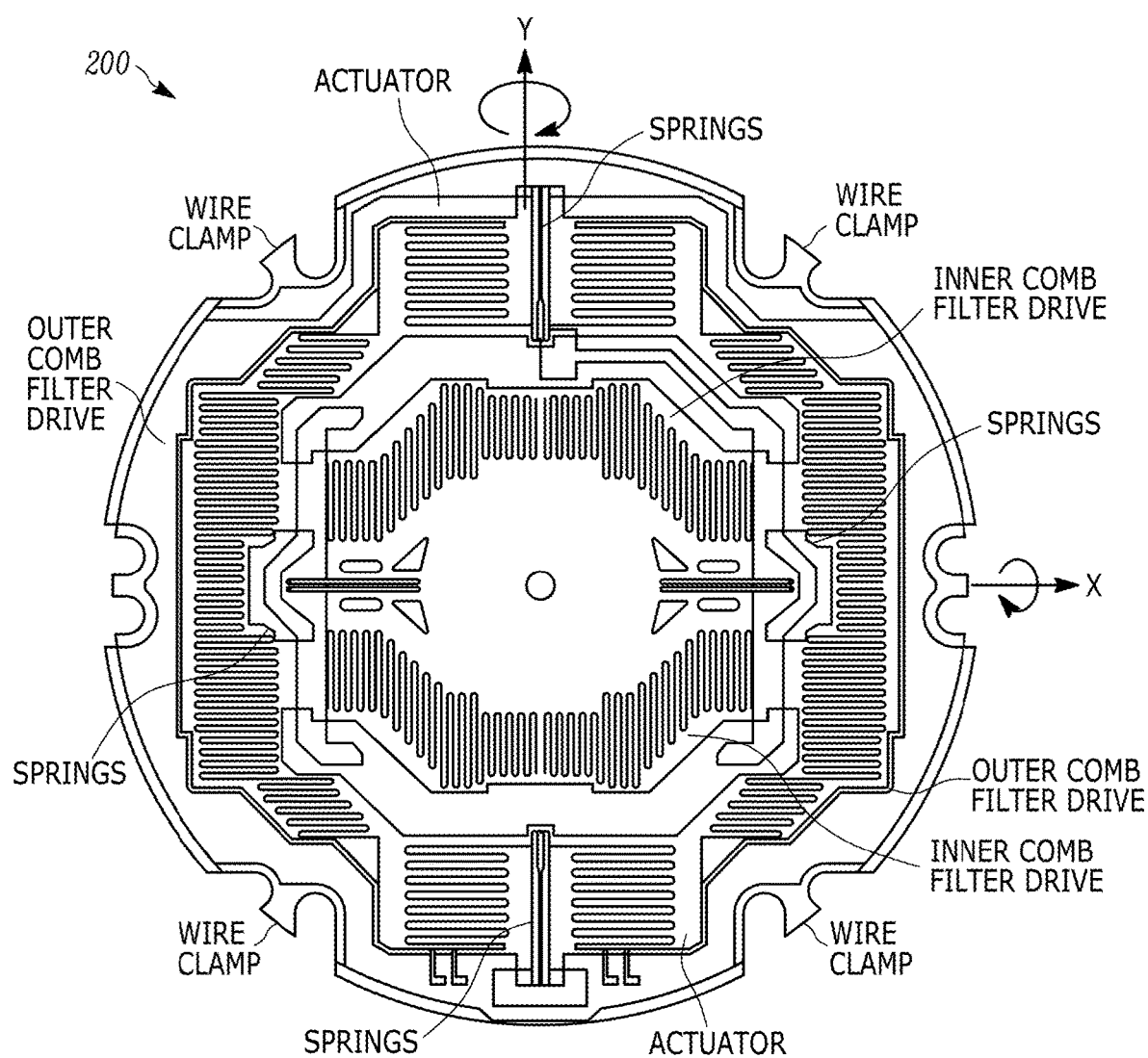
FIG. 3 is a top plan view of an example scanning unit for the single-axis confocal endomicroscope of FIG. 1

The scanning operations of an example implementation of the endomicroscope 102 are further discussed in reference to FIGS. 3, 4, 5, 6A, and 6B. FIG. 3 illustrates an example implementation of a MEMS scanning mirror assembly 200, which has an outer diameter of 2 mm in this example to allow for ultra-compact endomicroscope design. At the center of the MEMS assembly 200, in an example, the reflector mirror M1 has a 550 μm diameter. In an example, to fabricate the reflector surface of the mirror M1, Aluminum was sputtered on the front side of the MEMS assembly 200 to achieve reflectivity >90% between 400-700 nm. A 50 μm diameter aperture was etched in the center of the mirror M1 to allow the illumination beam exiting the SMF to pass. The mirror M1 is mounted on a gimbal frame.

To achieve ultra-compact design, a number of other design features were developed and implemented in some of the example endomicroscopes described herein. For example, the MEMS assembly 200 includes a plurality of wire clamp structures etched on edges of the MEMS assembly 200 to connect drive wires and to maintain the MEMS assembly 200 in place during operation, in particular during scanning. The drive wires may be wrapped around and or bonded to the wire clamps to provide a fixed anchor, even during scanning. Wire clamps substantially increased stability and endomicroscope longevity. In some examples, four wire clamp structures were used and in an opposing configuration, where each wire clamp structure has a paired wire clamp structure on an opposing side of the MEMS assembly 200 providing counterforce stability for the entire device during operation. Indeed, by having pairs of wire clamp structures in opposing configurations, the MEMS assembly 200 exhibits considerably low noise across the entire lateral scanning plane, i.e., across the X-axis and Y-axis.

Other design features include spring members that suspend the mirror M1 for rotational movement about the Y-axis as shown. In the illustrated example, two spring members are shown, one of each of side of the mirror M1. The two spring members are positioned on an outer region of an actuator configuration of the MEMS assembly 200.

In the illustrated example, the MEMS assembly 200 employs an actuator configuration that includes two actuating axes, about which, the mirror M1 may be independently rotated. The X-axis is defined as shown. The mirror M1 scans about the X-axis via an inner comb filter drive. The Y-axis is defined as shown, and the mirror M1 scans about the Y-axis using an outer comb filter drive. Inner and outer legs may be used and as part of the inner and outer comb filter drives, respectively. The inner and outer comb filter drives provide electrostatic actuation, such that the mirror M1 rotates around inner (X-axis) and outer (Y-axis) axes, respectively, when driven by drive signals. The comb filter drives are formed of electrostatic comb drive actuators disposed on sides of the M1 to provide driving forces that result in rotation of the M1. The comb filter drives may be configured to provide rotation in response to in-phase or out-of-phase drive signals, for example. The comb drive actuators may be serpentine springs, where the geometries of these springs may determine the resonant frequency(ies) for scanning.

Each of the inner and outer comb filter drives may be operated at a resonant frequency, e.g., a resonant frequency chosen to be between approximately 1 kHz and approximately 4 kHz, respectively. Furthermore, the MEMS assembly 200 may be driven with select resonant frequency drive signals to each comb drive, such that the mirror M1 undergoes a sinusoidal scanning pattern. In an example, the MEMS assembly 200 is driven by resonant frequencies to image at ≥5 frame/sec using a Lissajous scanning pattern, and scanning at 400×400 pixels per frame.

Figure 4:
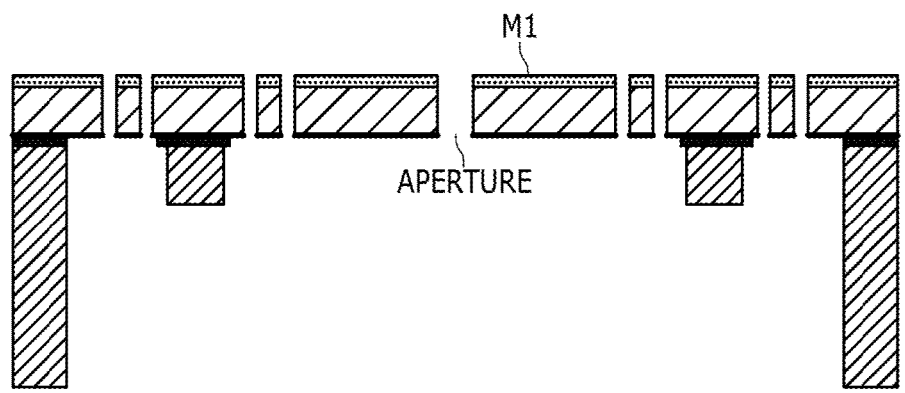
FIG. 4 is a side view of a deep reactive-ion etching (DRIE) process used to form the scanning unit of FIG. 3, in accordance with an example.
Figure 5:
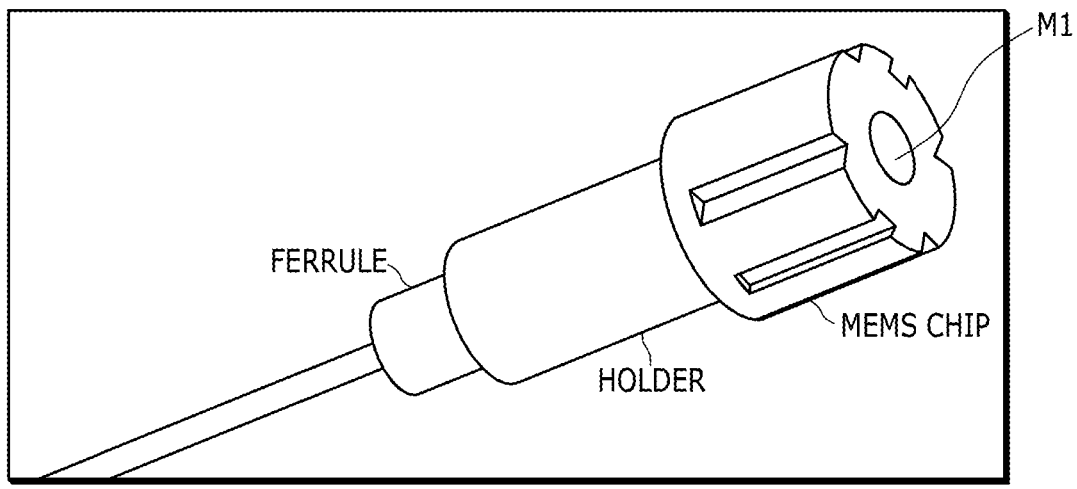
FIG. 5 illustrates an endomicroscope having a scanning unit assembled onto a holder and secured with a ferrule, in accordance with an example.

FIG. 4 illustrates an example deep reactive-ion etching (DRIE) process profile used to form the MEMS assembly 200, in an example. In an example, the MEMS assembly was fabricated using a silicon-on-insulator 3 step deep reactive-ion etch DRIE process with 3 masks. FIG. 5 illustrates an example endomicroscope having the MEMS assembly 200 (labeled a MEMS chip) at a distal end mounted in place on a 2 mm outer diameter holder connected to an optical fiber through a ferrule, as shown.

Figure 6A:
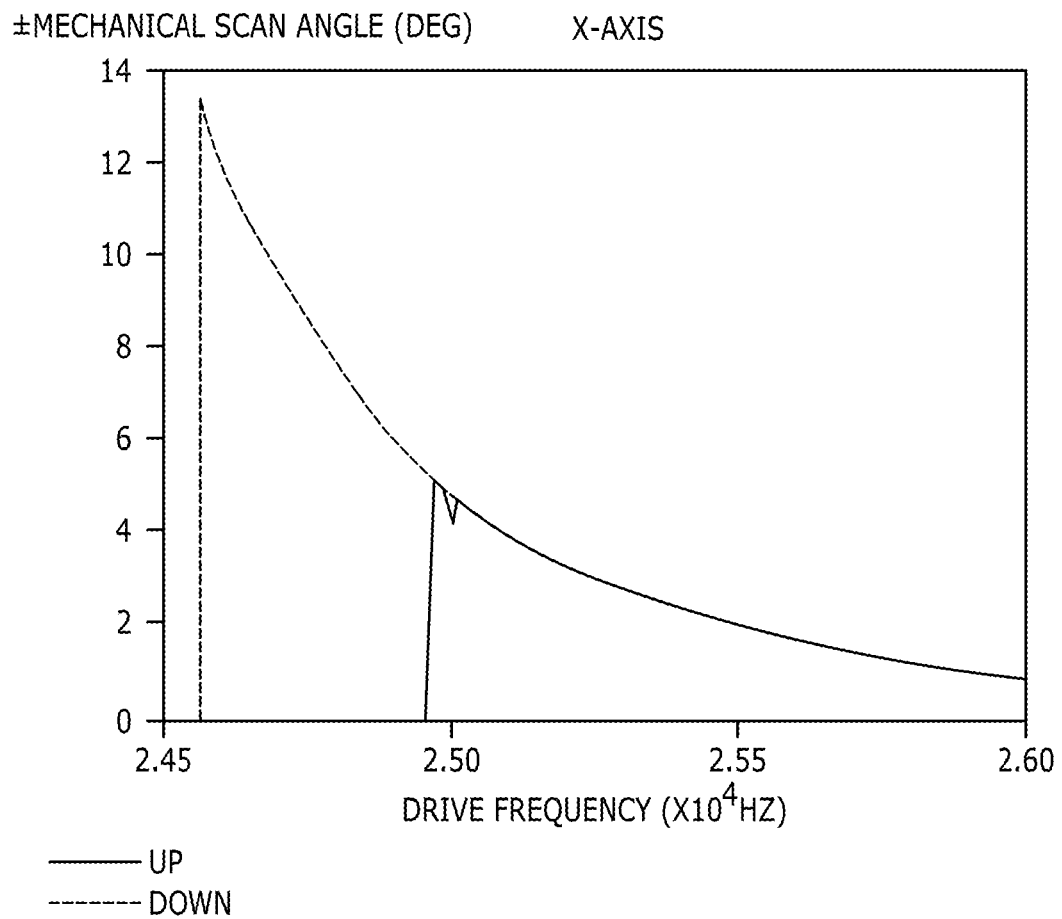
FIGS. 6A and 6B are plots of frequency response of an x-axis and a y-axis of the scanning unit of FIG. 3, in accordance with an example.
Figure 6B:
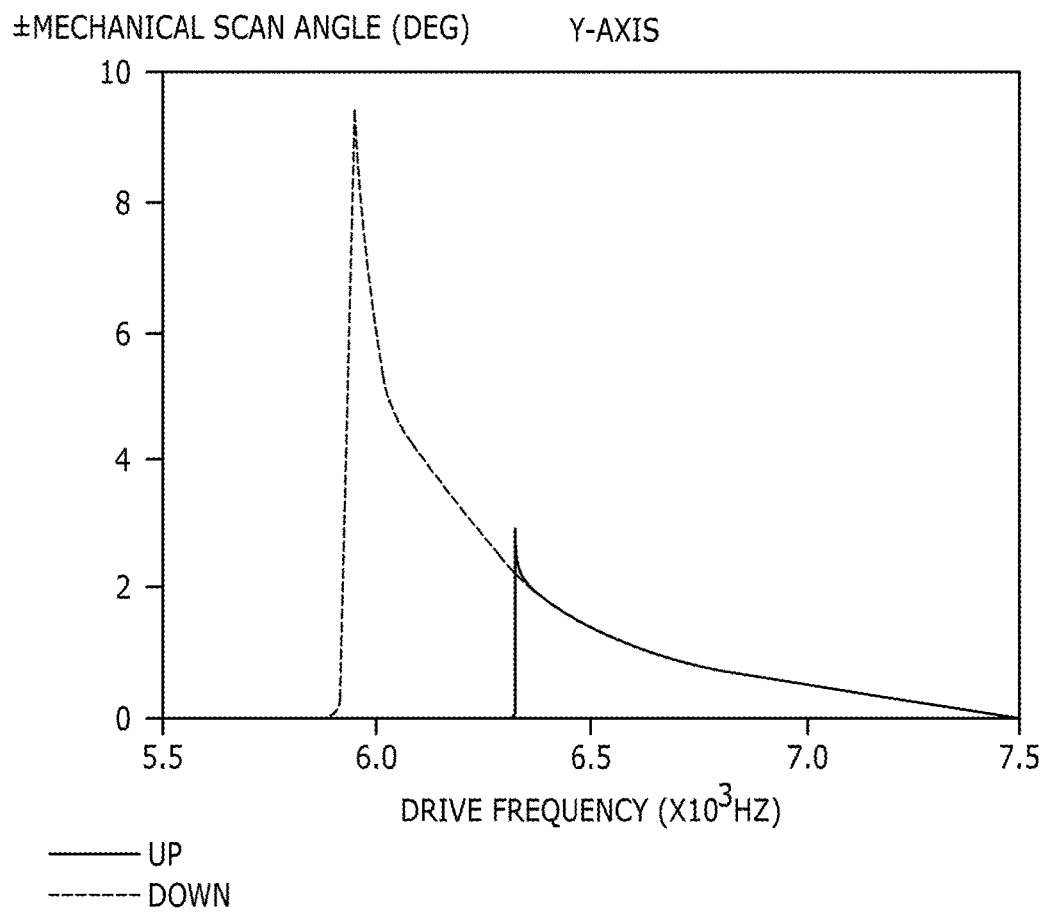

FIGS. 6A and 6B are plots of frequency response of an X-axis and Y-axis of the MEMS assembly 200. A large scan angle can be achieved for M1 by sweeping the drive signal from high-to-low frequencies (downsweep) in either the X- or Y-axes, as shown in FIGS. 6A and 6B, respectively. Sweeping in the opposite direction from low-to-high frequencies (upsweep) generates a smaller scan angle. In some examples, drive frequencies were selected to generate a dense Lissajous scan pattern at a high repetition rate. In an example, sine waves with amplitude of 60 $V_{pp}$ and frequencies near 24 kHz and 6 kHz were used and resulted in tilt frequencies of 12 kHz and 3 kHz for the X- and Y-axes, respectively. A field of view (FOV) of 350×350 µm² was generated that was covered by either 300×300 or 400×400 pixels at either 20 or 10 frames per sec, respectively, with a pixel spacing of either 1.17 or 0.875 µm, respectively. Motion artifacts could be reduced by imaging at higher speeds, but with fewer pixels.

Figure 7A:
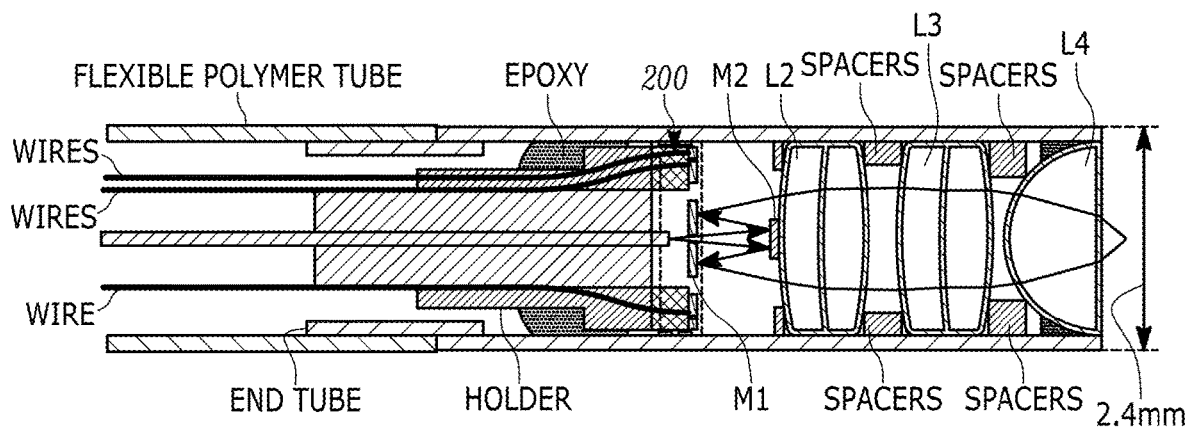
FIG. 7A illustrates a cross-sectional side view of a single-axis confocal endomicroscope, in accordance with an example.

FIGS. 7A-7E provide different cross-sectional views of an assembled distal end of the endomicroscope 102, in an example implementation. The distal end of the endomicroscope 102 was secured in a stainless steel outer tube with 2.4 and 2.0 mm outer diameter (OD) and inner diameter (ID), respectively, and with a 10 mm length, as shown in FIG. 7A. The MEMS holder is used to hold the MEMS assembly 200 in alignment with the fiber ferrule, as shown. In particular, the SMF is axially aligned with the center aperture of mirror M1, as a result of the MEMS holder. In an example, the scanner was isolated from unwanted mechanical vibrations by inserting a 3 mm long stainless steel end tube with 2.0 and 1.6 mm OD and ID, respectively, was inserted between the rigid outer tube and the flexible tubing to mechanically isolate the MEMS assembly 200, and in particular the scanning mechanism, from unwanted vibrations.

In some examples, the MEMS assembly 200 may include a position sensing detector (PSD) configured to measure tilt angles about one or both of the X-axis and the Y-axis during scanning. The PSD can, therefore, detect misalignment errors where the illumination beam is not longer aligned with the aperture in M1. In other examples, the comb filter drives may be driven in a closed-loop control configuration that allows a MEMS driver to determine scanning angle for scanning and for preventing misalignment. In some examples, piezoresistive sensors may be coupled to the actuators of the comb filter drives to provide an indication of scanning angle. With closed-loop control, such sensors can provide feedback that the MEMS driver uses for adjusting drive signals to achieved desired scanning with M1.

Figure 7B:
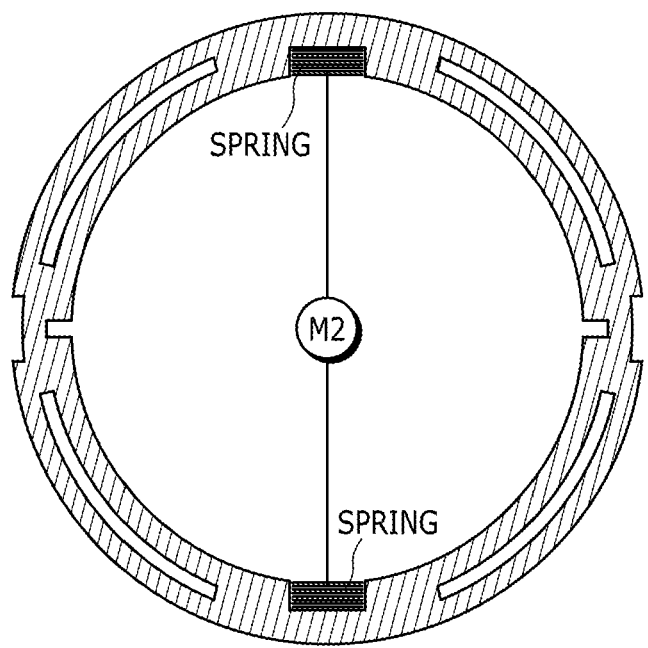
FIGS. 7B-7D illustrate cross-sectional views of the single-axis confocal endomicroscope of FIG. 7A, taken at different positions of the endomicroscope, in accordance with an example.
Figure 7C:
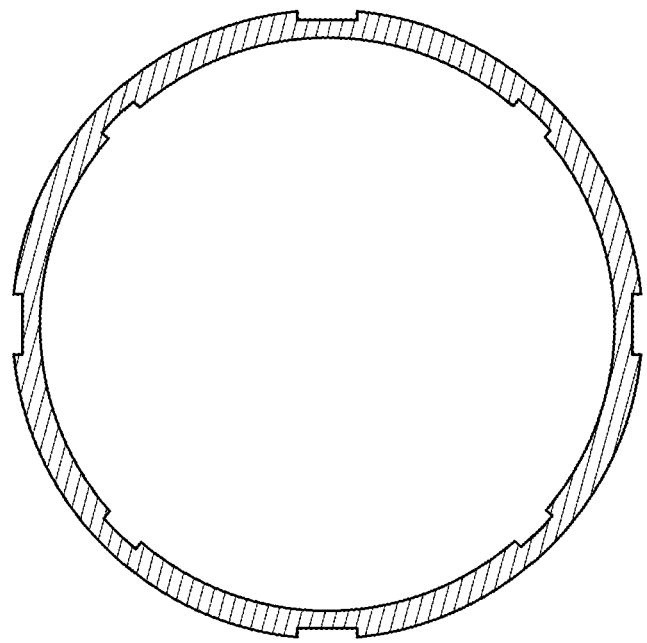
Figure 7D:
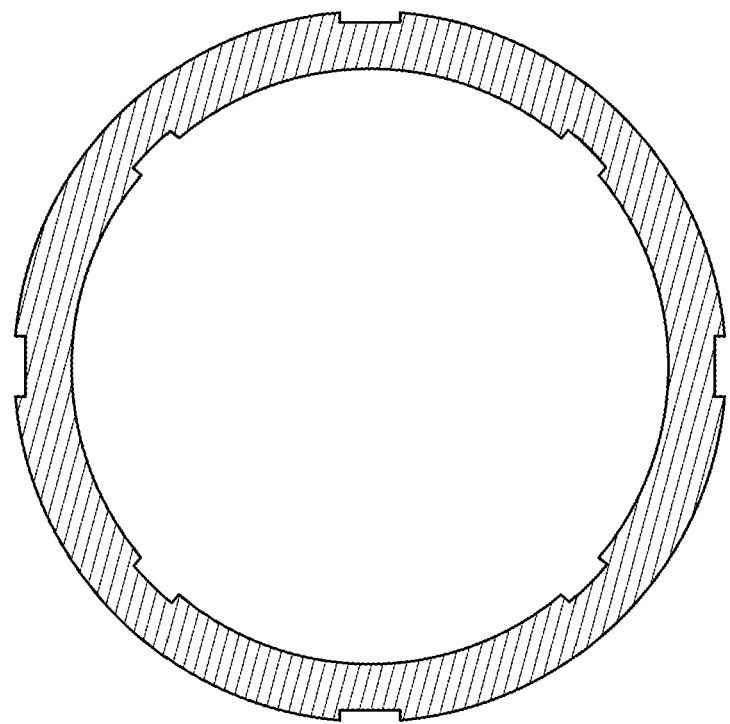
Figure 7E:
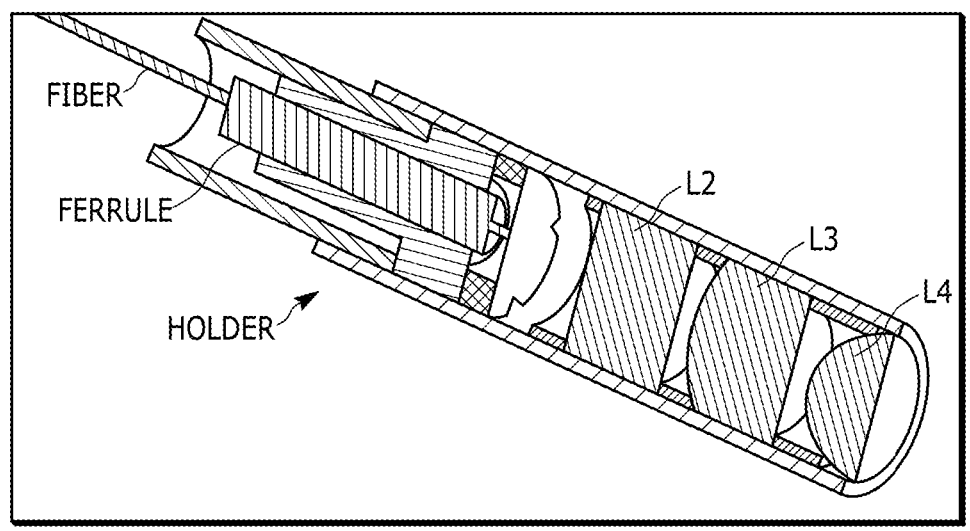
FIG. 7E illustrates a cross-sectional, perspective view of a schematic of the single-axis confocal endomicroscope of FIG. 7A, in accordance with an example.
Figure 8:
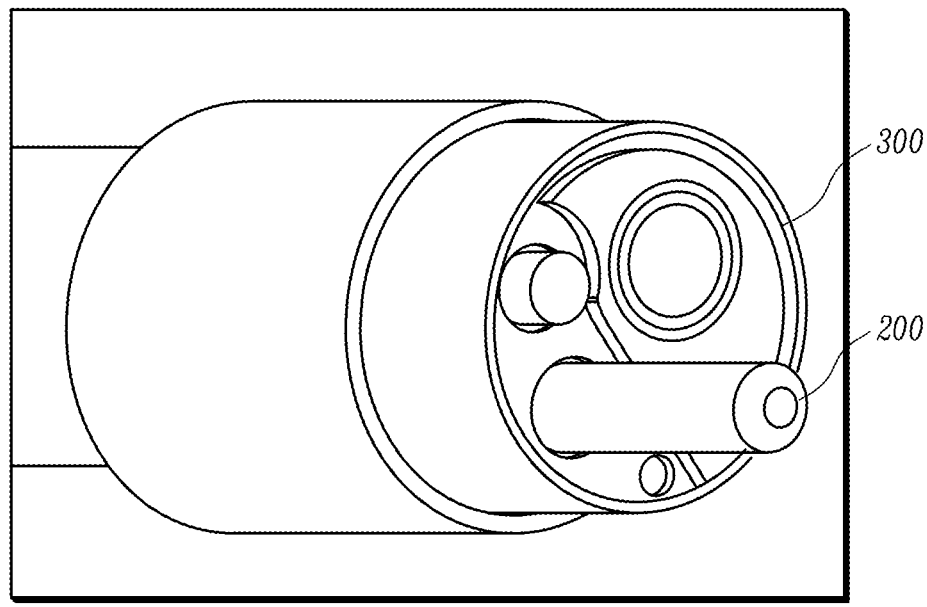
FIG. 8 illustrates an ultra-compact medical imaging endoscope having a standard 2.8 mm diameter for optical biopsy and implemented with a single-axis confocal endomicroscope, in accordance with an example.

Micromachining methods were used to fabricate the fixed mirror M2 and the spacers used to mount the distal optics, L2-L3, shown. The top surface of the fixed mirror M2 is coated with a ~70 nm Aluminum layer to achieve >90% reflectivity at 488 nm. The diameter of 0.29 mm covers the dimensions of the illumination beam, and is designed to fully cover the beam exiting from the SMF and achieve >80% fluorescence collection efficiency. For easy handling and precise assembly of this tiny component, the fixed mirror M2 is supported by a 8 µm wide straight bar, via a pair of flexible springs connected to the annular frame, as shown in FIG. 7B. The OD and ID of that annular frame (FIG. 7B) were 1.97 and 1.6 mm, respectively, and were designed to match the optics without blocking either the illumination or output beams. The OD and ID of the spacer between lenses L2 and L3 were 1.97 mm and 1.8 mm, respectively, as shown in FIG. 7C. The OD and the ID of the spacer between lenses L3 and L4 were 1.97 mm and 1.7 mm, respectively, as shown in FIG. 7D. All of the spacers were fabricated on a silicon wafer with a thickness of 0.5 mm. The distance between the MEMS assembly and optics was adjusted by moving the MEMS assembly with a 3D translational stage to achieve a WD=50 µm. FIG. 7E illustrates a cutaway view of an example configuration. FIG. 8 illustrates a medical endoscope 300 having an inner diameter channel, in particular a 2.8 mm ID instrument channel, through which the ultra-compact single-axis endomicroscope 102 has been drawn. In an example, the medical endoscope 200 was an Olympus GIF-HQ190 endoscope.

Figure 9A:
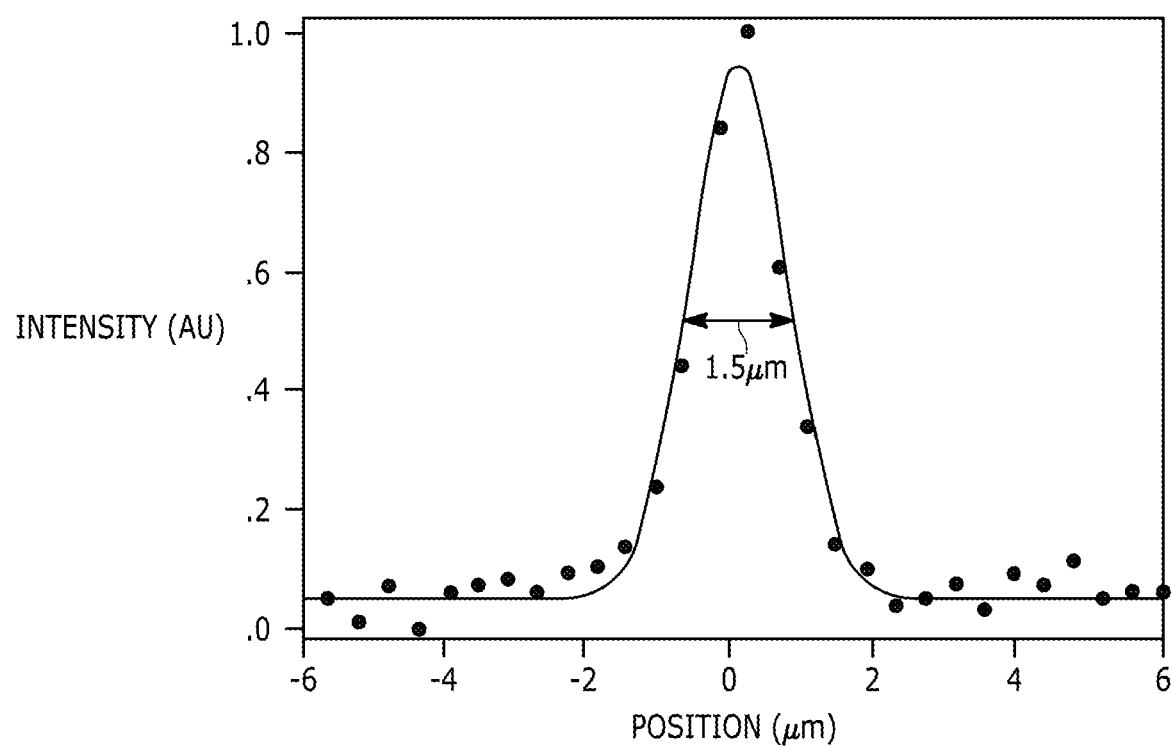
FIGS. 9A and 9B illustrate plots of the full-width half maximum (FWHM) of showing sub-resolution (100 nm) fluorescent beads using optical elements L2, L3, and L4 in single-axis confocal endomicroscope design, along lateral (FIG. 9A) and axial (FIG. 9B) directions, showing resolutions of 1.5 µm and 12 µm, respectively, in accordance with an example.
Figure 9B:
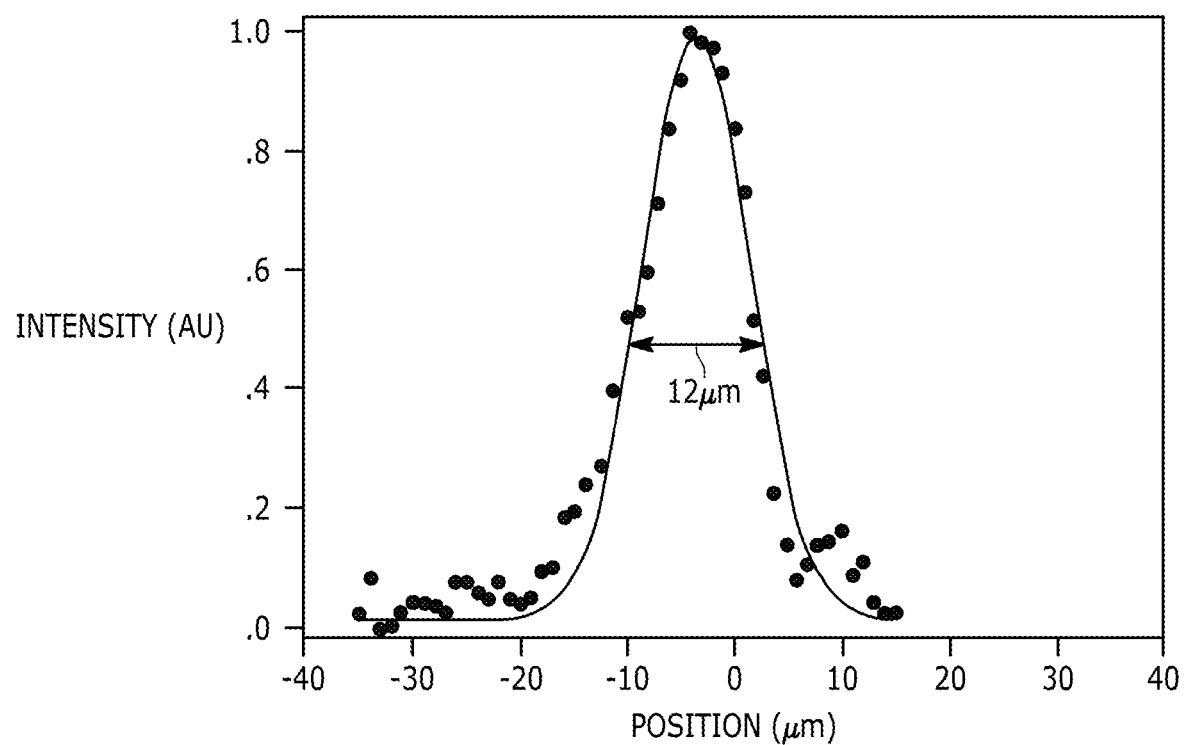
Figure 9C:
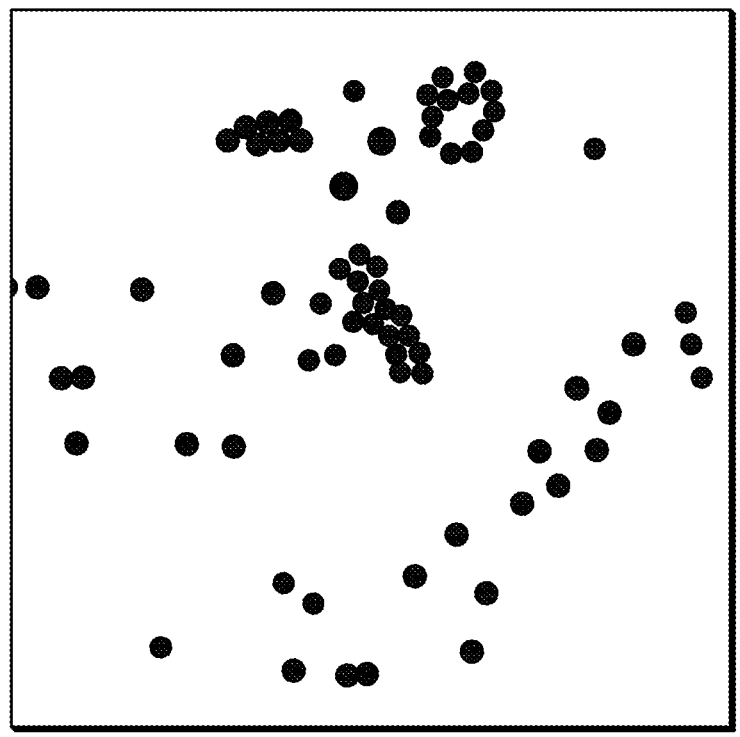
FIG. 9C is an image of dispersed 10 mm beads showing a field of view (FOV) of 350×350 µm$^2$, in accordance with example.

FIGS. 9A and 9B illustrate plots of the full-width half maximum (FWHM) of showing sub-resolution (100 nm) fluorescent beads using optical elements L2, L3, and L4 in the single-axis confocal endomicroscope 102, along lateral (FIG. 9A) and axial (FIG. 9B) directions, showing resolutions of 1.5 µm and 12 µm, respectively. FIG. 9C shows that an image of dispersed 10 mm beads in a sample use of the endomicroscope showing a FOV of 350×350 µm².

Example

Figure 10A:
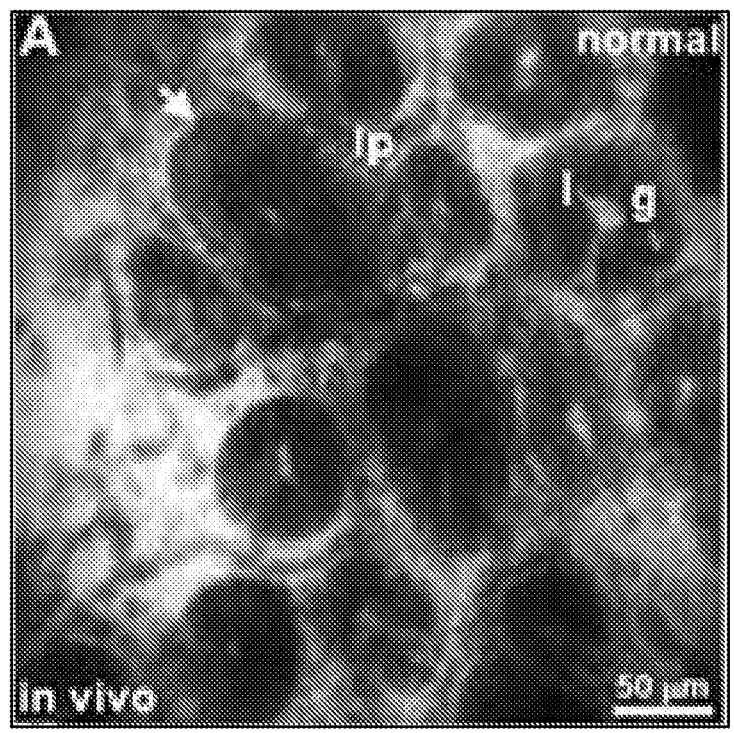
FIGS. 10A and 10B are in vivo fluorescence images of mice colon taken with a single-axis confocal endomicroscope and showing a normal colon (FIG. 10A) and a dysplasia in CPC; Apc colon (FIG. 10B), in accordance with an example.
Figure 10B:
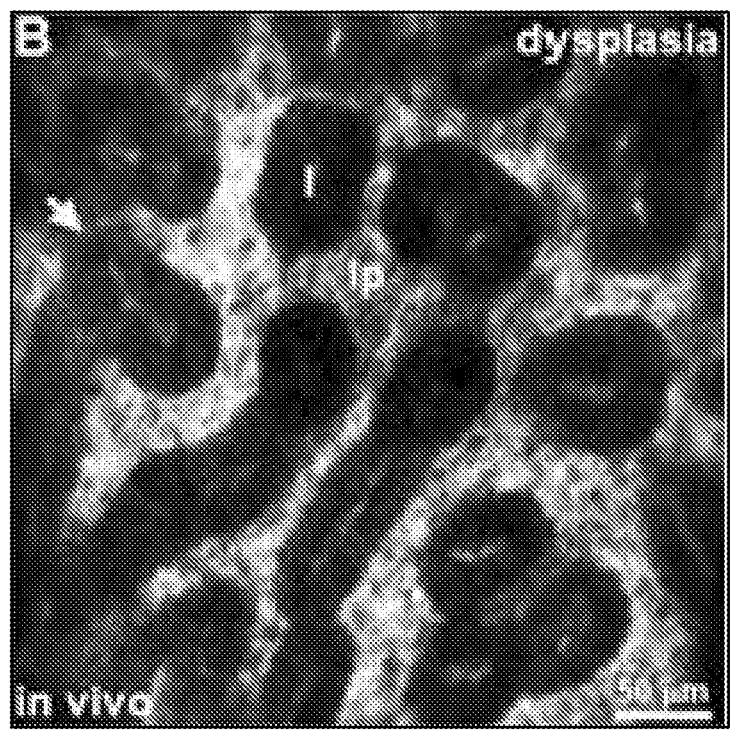
Figure 10C:
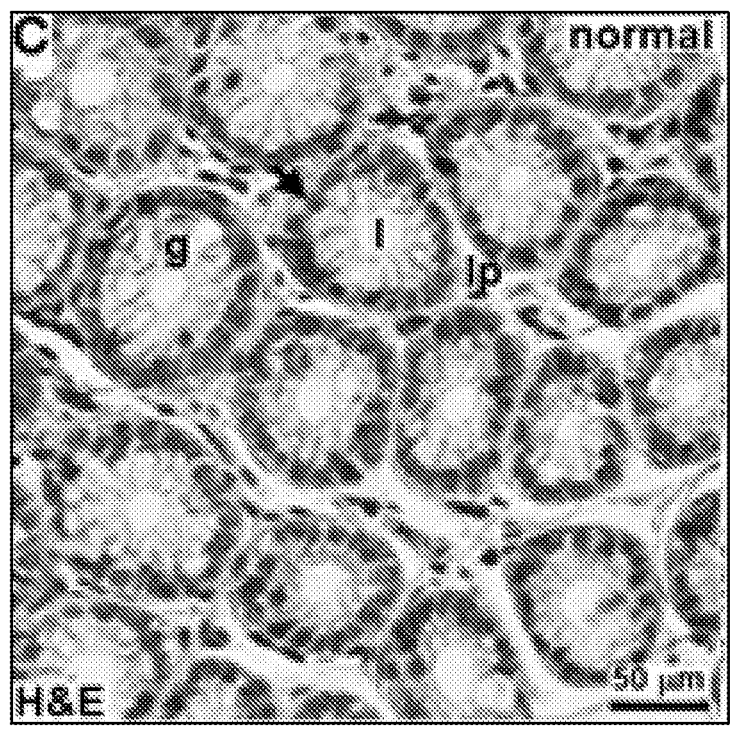
FIGS. 10C and 10D are histological (H&E) images for a normal colon (FIG. 10C) and for a colon with dysplasia (FIG. 10D), in accordance with an example.
Figure 10D:
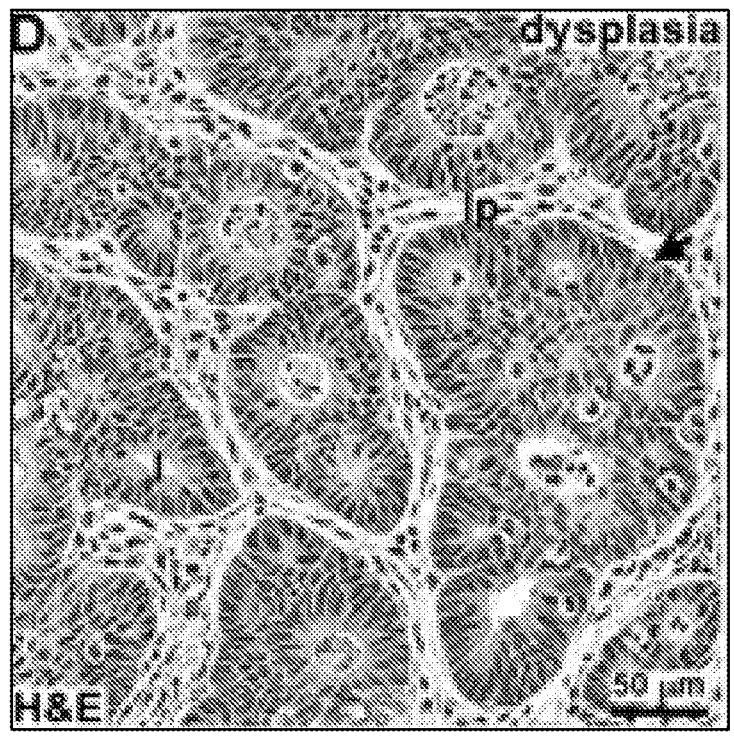
Figure 11A:
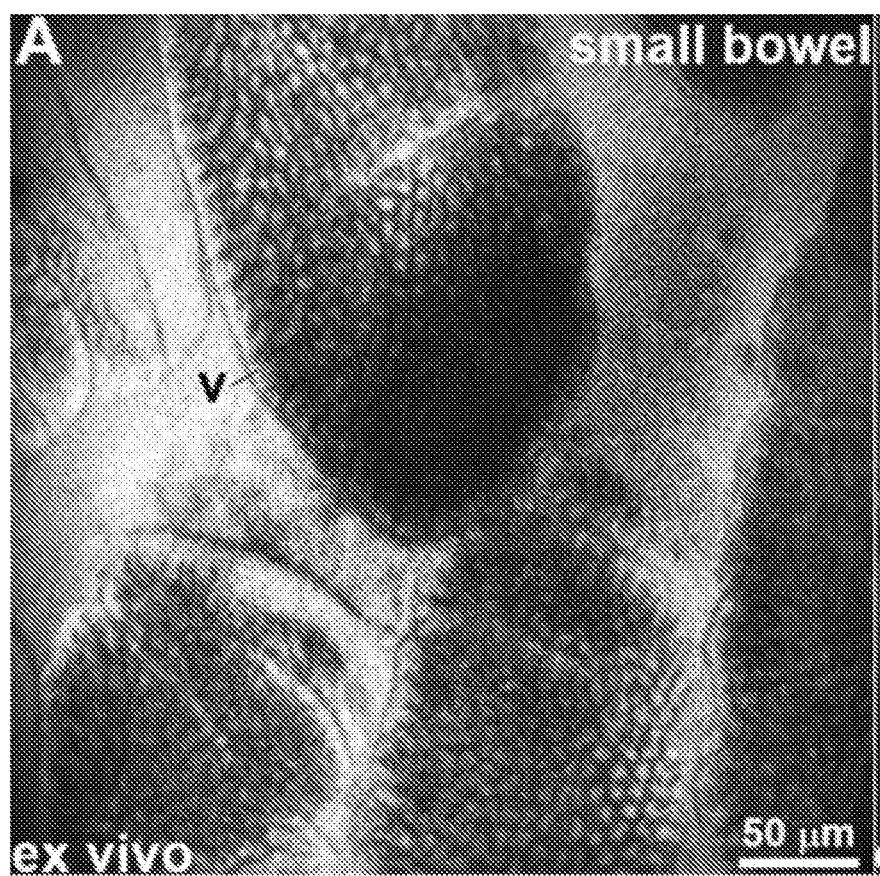
FIGS. 11A and 11B are ex vivo fluorescence images of mice taken with a single-axis confocal endomicroscope and showing the presence of villi (v) in the small bowel (FIG. 11A) and showing a kidney with renal tubule (t) and glomerulus (g) (FIG. 11B), in accordance with an example.
Figure 11B:
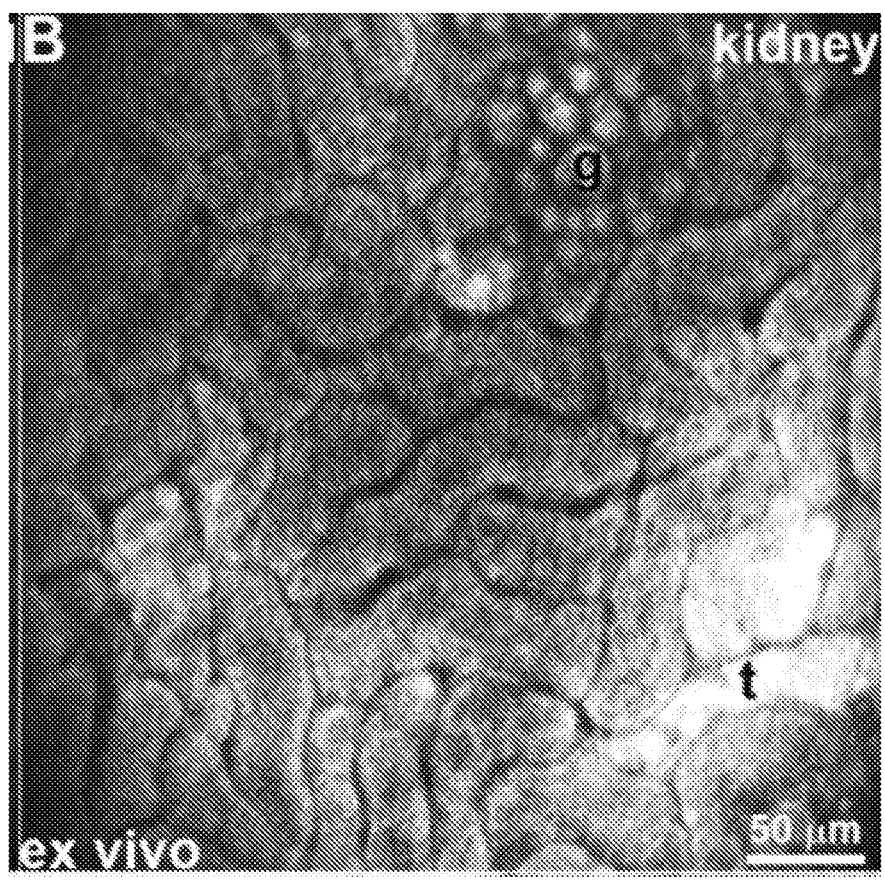
Figure 11C:
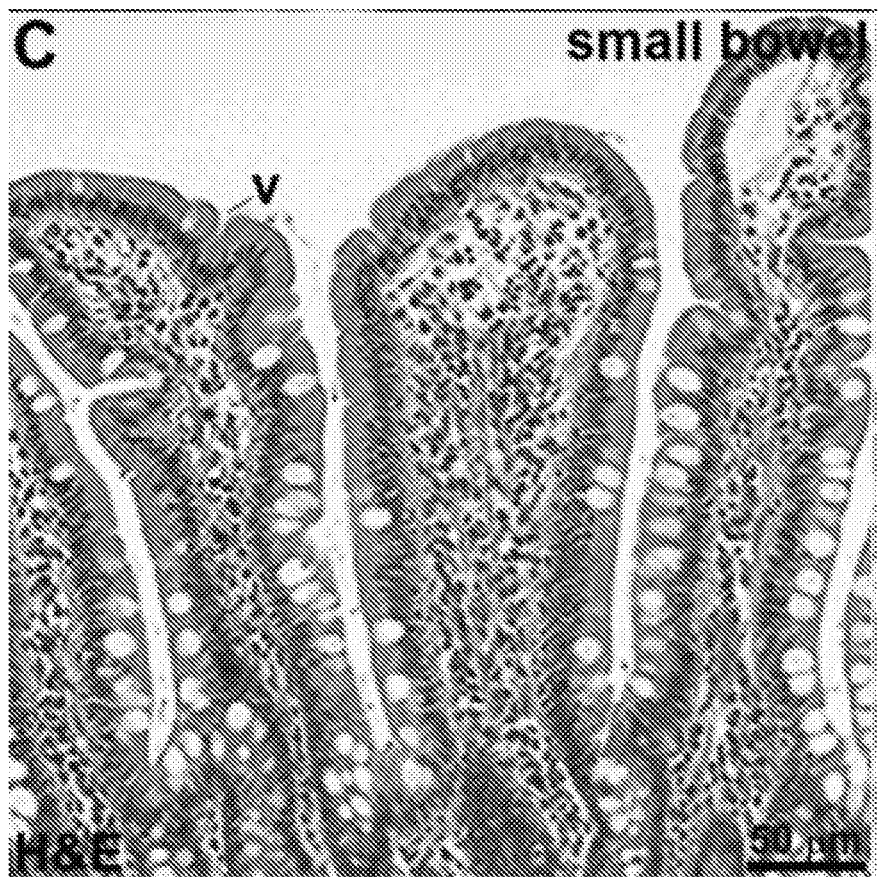
FIGS. 11C and 11D are histological (H&E) images of the small bowel and kidney, respectively.
Figure 11D:
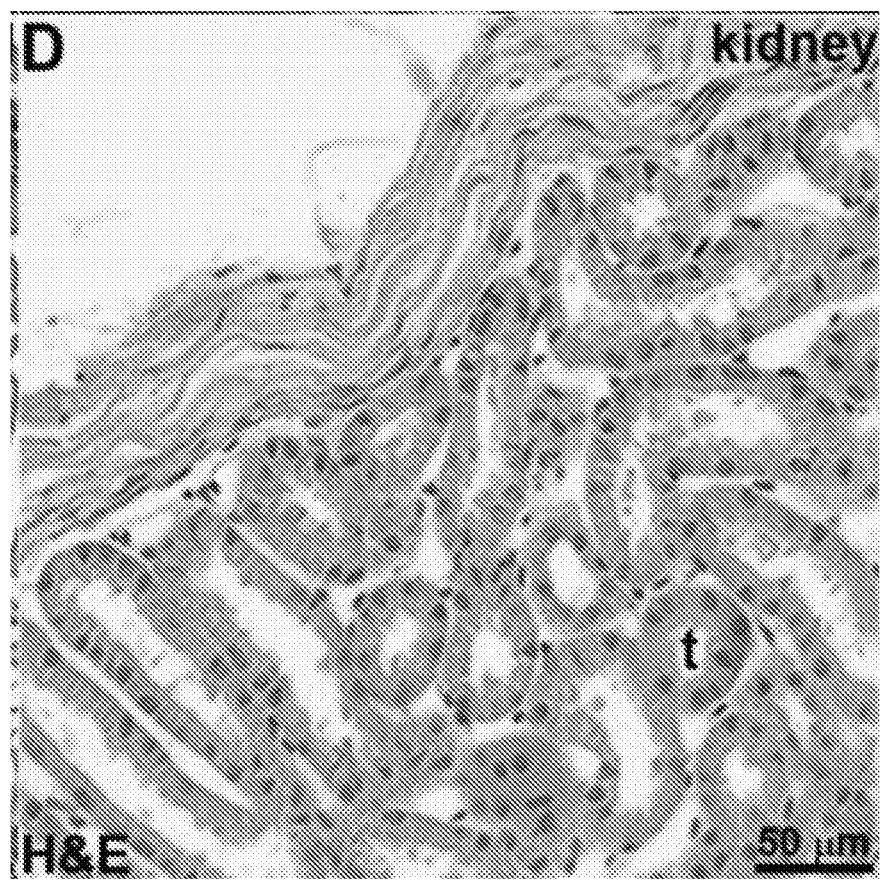

With a $\lambda_{ex}$=488 nm excitation, an ultra-compact single-axis confocal endomicroscope in accordance with the present teachings was used to collect fluorescence images in vivo from the colon of CPC; Apc mice. Representative images of normal and dysplasia are shown following intravenous injection of fluorescein, FIGS. 10A and 10B. Distinct crypt structures (arrow) with central lumen (l), goblet cells (g), and surrounding lamina propria (lp) can be identified in the images. Representative histology hematoxylin and eosin (H&E) stain images are shown for normal and dysplasia, FIGS. 10C and 10D, respectively.

Fluorescence images collected ex vivo, using a ultra-compact single-axis confocal endomicroscope in accordance with examples herein, are shown in FIGS. 11A-11D. The images from small bowel show villi and from kidney show renal tubules and glomeruli, see, FIGS. 11A and 11B, respectively. Representative histology hematoxylin and eosin (H&E) stain images are shown for normal and dysplasia small bowel, in FIGS. 11D and 11D, respectively.

In some examples, confocal images may be reconstructed in accordance with a Lissajous scan pattern. The time series of discrete data may be mapped as intensities to each pixel location. The Lissajous trajectory may be determined by the scan frequencies $f_x$, $f_y$, and phase delays $\varphi_x$, $\varphi_y$ between the input drive voltage and the sinusoidal motion of the mirror in the X- and Y-axes. The pixel location (x, y) may be mapped using the following equations, where $P_x$, $P_y$ represent the image dimensions in terms of pixels:

$$x(t)=\tfrac{1}{2}P_x[\sin(2\pi f_x t+\varphi_x)+1]$$

$$y(t)=\tfrac{1}{2}P_y[\sin(2\pi f_y t+\varphi_y)+1]$$

In these examples, the Lissajous scan patterns are sparse in the center of the image and increased in density towards the periphery. Unsampled pixels (empty spaces where beam is not scanned) may be calculated by counting the number of pixels with intensity of zero. These unsampled pixels are filled in with the average intensities of eight neighboring pixels, with the process performed in real time during in vivo imaging. Thus, in these examples, dense scan regions resulted in assigning multiple intensity values to a pixel that are averaged to obtain the processed image.

Figure 13A:
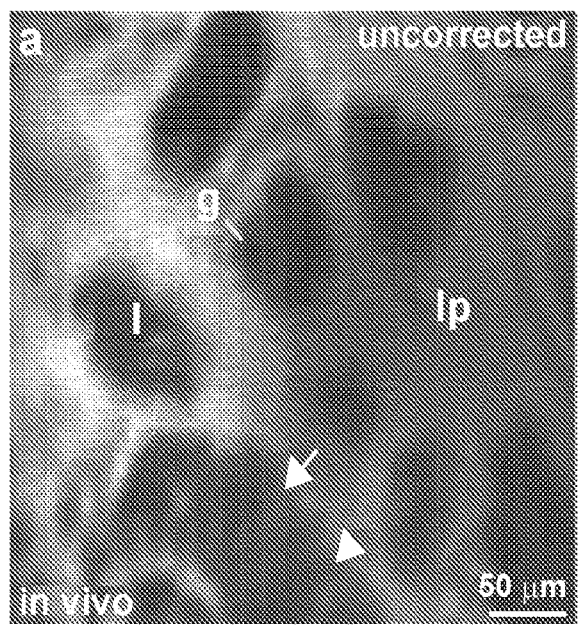
FIG. 13A is an image showing blurring results from misregistered pixels in an uncorrected confocal image collected in vivo from mouse colon, in an example.
Figure 13B:
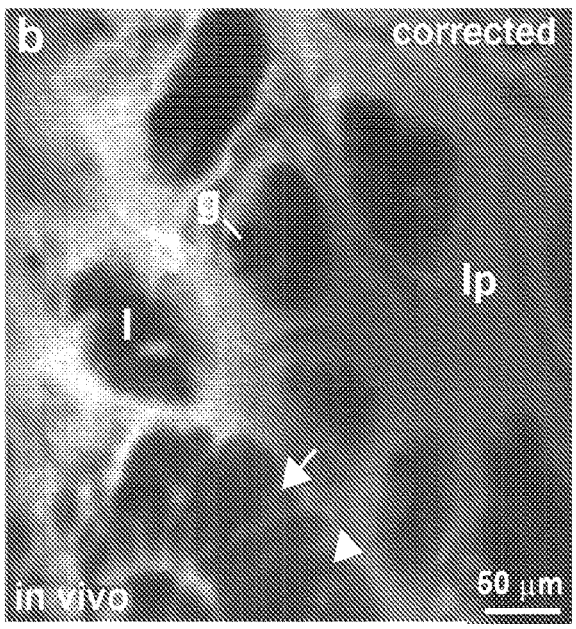
FIG. 13B is an image after phase correction, sub-cellular features, including cell membrane (arrow) from an adenomatous crypt (arrowhead), and goblet cells (g) can be distinguished.

In some examples, the deflection amplitude and phase delay of the scan mirrors versus drive voltage were calibrated in the laboratory under ambient conditions prior to in vivo imaging. These parameters may drift over time after the instrument is inserted into a subject. In vivo images can appear blurry due to perturbations in phase delay from environmental effects on the scan mirror dynamics, such as variations in temperature, as a result. In some examples, these phase shifts can cause errors in assignment of intensity values to pixel locations. The actual phase delay of the scanner during in vivo use was recovered using a phase correction algorithm by optimizing a sharpness metric S defined by following equation:

$$S = \frac{1}{MN}\sum_i^M \sum_j^N (I(i,j) - I_{avg})^2$$

where, I(i, j) are the gray scale intensities of the reconstructed image, and $I_{avg}$ is the average of all the pixel intensities in the image. M and N are the total number of pixels along the height and width of the image. The phase corresponding to the sharpest image was selected as a new estimate for subsequent reconstruction of images and videos. Phase correction may be performed either at regular time intervals or as needed. The resulting images were further processed using gamma correction to enhance image brightness and contrast. In an example, a wiener filter was used to reduce shot and Gaussian noise from PMT and amplifier. This filter can suppress noise without blurring to minimize image degradation. In some experiments, phase shifts observed during the in vivo experiments were ~2-3°. Correction resulted much sharper images whereby sub-cellular features could be distinguished, see, FIG. 13A in comparison to FIG. 13B. Thus, phase correction can be made without loss of image quality during in vivo imaging.

Figure 12:
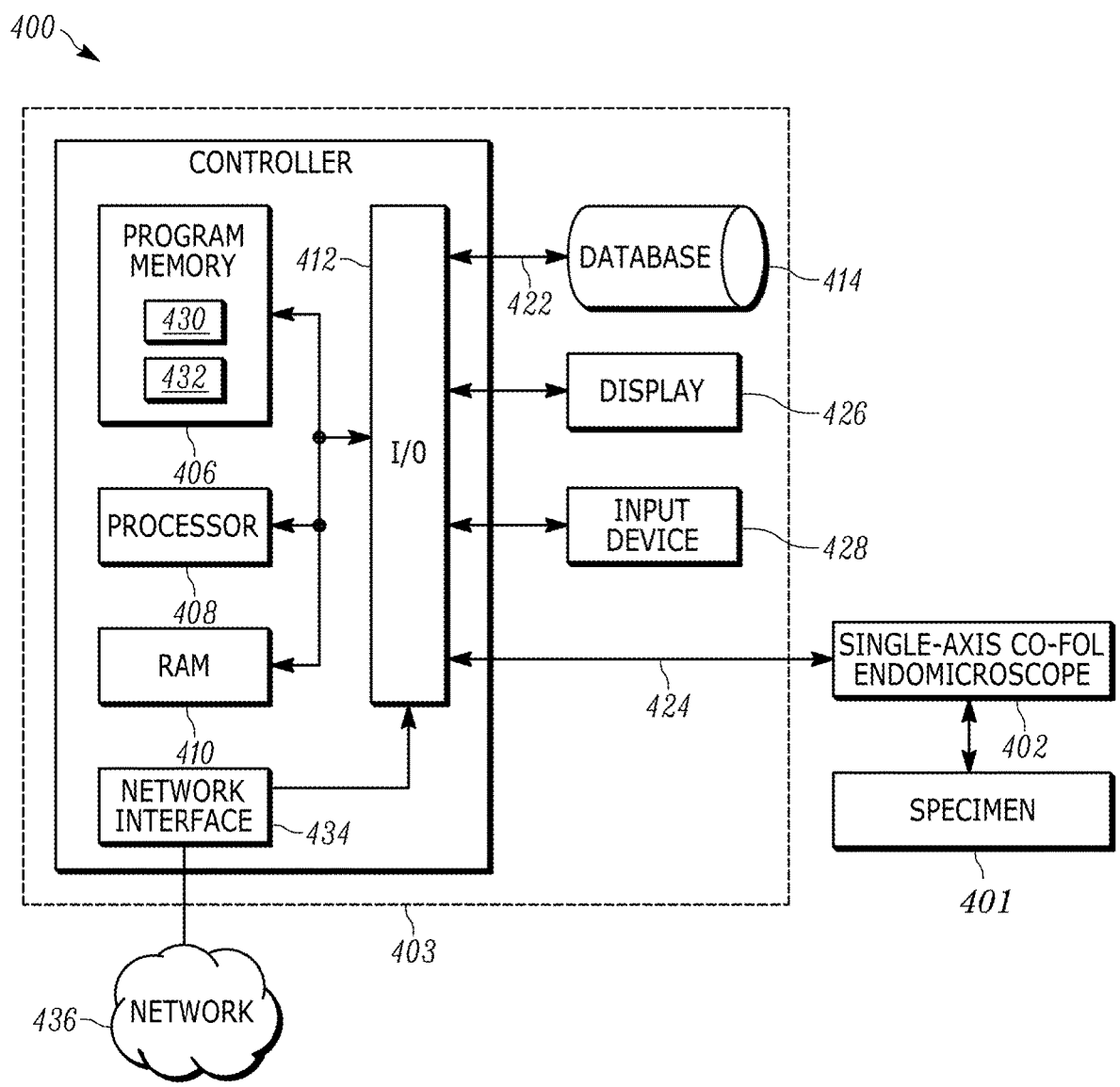
FIG. 12 depicts an example block diagram of an example single-axis endomicroscope system, in accordance with an example.

FIG. 12 is an example block diagram 400 illustrating the various components used in implementing an example embodiment of a single-axis confocal endomicroscope system. The single-axis confocal endomicroscope 402 may be positioned adjacent or operatively coupled to a specimen 401. The control device 403 may have a controller 404 operatively connected to a database 414 via a link 422 connected to an input/output (I/O) circuit 412. It should be noted that, while not shown, additional databases may be linked to the controller 404 in a known manner. The controller 404 includes a program memory 406, a processor 408 (which may be a microcontroller or a microprocessor), a random-access memory (RAM) 410, and the input/output (I/O) circuit 412, all of which are interconnected via an address/data bus 420. It should be appreciated that although only one microprocessor 408 is shown, the controller 404 may include multiple microprocessors 408. Similarly, the memory of the controller 404 may include multiple RAMs 410 and multiple program memories 406. Although the I/O circuit 412 is shown as a single block, it should be appreciated that the I/O circuit 412 may include a number of different types of I/O circuits. The RAM(s) 410 and the program memories 406 may be implemented as semiconductor memories, magnetically readable memories, and/or optically readable memories, for example. A link 424 may operatively connect the controller 404 to endomicroscope 402 through the I/O circuit 412. The I/O circuit 412 may be connected to a network interface 434 that provides a wired or wireless connection to a network 436.

The program memory 406 and/or the RAM 410 may store various applications (i.e., machine readable instructions) for execution by the microprocessor 408. For example, an operating system 430 may generally control the operation of the endomicroscope 402 and provide a user interface to the testing apparatus to implement the processes described herein. The program memory 406 and/or the RAM 410 may also store a variety of executive instructions 432 for accessing specific functions of the endomicroscope 402. By way of example, and without limitation, the executive instructions 432 may include, among other things: instructions for controlling operation of the endomicroscope 402, or other endoscopic device, as described herein; instructions for capturing images with the endomicroscope 402 as described herein; and other instructions, for example, implementing software keyboard functionality, interfacing with other hardware in the endomicroscope 402, etc. The program memory 406 and/or the RAM 410 may further store data related to the configuration and/or operation of the endomicroscope 402, and/or related to the operation of one or more instructions. For example, the data may be data gathered by the endomicroscope 402, data determined and/or calculated by the processor 408, etc. In addition to the controller 404, the endomicroscope 402 may include other hardware resources. The endomicroscope 402 may also be coupled to various types of input/output hardware such as a visual display 426 and input device(s) 428 (e.g., keypad, keyboard, etc.) to fine tune actuation of the lateral scanning. In an embodiment, the display 426 is touch-sensitive, and may cooperate with a software keyboard routine as one of the software routines 432 to accept user input.

The present techniques provide an ultra-compact design for microsystems-based confocal endomicroscopes. With the present techniques, a 2.4 mm diameter microsystems-based confocal laser endomicroscopy capable of passing easily through the 2.8 mm biopsy channel of a standard medical endoscope can be achieved. To our knowledge, this is the smallest caliber microsystems-based instrument to date. The ultra-compact distal end contains a fast MEMS scanner and condensed lens assembly packaged in a short rigid length of 10 mm and 2 mm diameter to navigate the large bending angle at the entry of the channel.

The optical design uses a folded path to expand the beam and achieve NA=0.41 for diffraction-limited resolution on-axis. Using intravenous fluorescein, real-time images can be collected from tissue in vivo (or in some examples ex vivo) to distinguish normal from pre-malignant (dysplasia) mucosa, for example, using intravenous fluorescein for contrast. The resulting endomicroscopes can be used at the point-of-care to avoid the long processing times required by physical biopsies and provide physicians with instant pathology feedback during the procedure.

The ultra-compact form factors provided herein are compatible with a wide range of medical endoscopes used by community physicians, and can be used for a broad range of clinical applications.

We demonstrate advances in microsystems packaging to scale down the dimensions of the instrument for endoscope compatibility. The MEMS chip, for example, may be designed with wire clamp structures rather than bond pads to facilitate connection and pass though of the drive and signal wires. Further, the drive signal to the scanner may be tuned to achieve a mixed softening/stiffening effect to increase the mechanical scan angle and hence performance of the reflector. Microfabrication techniques were used to produce spacers with stringent tolerances to align optics. Further, an end tube is inserted to isolate the scanner from bending motions incurred by the flexible tubing that protects the optical fiber. Thus, the large stresses that occur when an endomicroscope is passed through the instrument channel for in vivo imaging are compensated for.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An endomicroscope assembly comprising:
   a flexible tubing having a ferrule and single-mode optical fiber extending into the ferrule, the flexible tubing having a distal end positioned to emit an illumination beam provided when provided to the single-mode optical fiber;
   a compact scanning assembly mounted to the flexible tubing, the compact scanning assembly having a folded beam configuration to receive the illumination beam, to convert the illumination beam to a higher numerical aperture illumination beam, and to scan the higher numerical aperture illumination beam across a lateral sample region, the compact scanning assembly comprising:
      a rigid outer housing;
      a lateral scanning assembly fixedly positioned within the rigid outer housing and adjacent the distal end of the flexible tubing, the lateral scanning assembly having a scanning mirror with an aperture aligned with the single mode fiber to receive the illumination beam into a folded beam path for converting to the higher numerical aperture illumination beam, the folded beam path being defined by the scanning mirror and a fixed mirror, the laser scanning assembly having a comb filter drive for scanning the scanning mirror;
      a lens assembly fixedly positioned within the rigid outer housing, the lens assembly positioned distally to the lateral scanning assembly to scan the higher numerical aperture illumination beam across the later sample region; and
      a spacer fixedly positioned within the rigid outer housing and distally to the lateral scanning assembly, the spacer having spring members that fixedly suspend the fixed mirror.

2. The endomicroscope assembly of claim 1, wherein the lateral scanning assembly further comprises one or more wire clamping elements for fixed attaching drive wires connecting the lateral scanning assembly with a scan driver processing unit.

3. The endomicroscope assembly of claim 1, wherein the lens assembly comprises a plurality of lens elements and one or more secondary spacers positioned to space apart adjacent lens elements.

4. The endomicroscope assembly of claim 3, wherein the plurality of lens elements comprises two achromatic doublet lenses.

5. The endomicroscope assembly of claim 4, wherein the plurality of lens elements comprises a plano-convex lens.

6. The endomicroscope assembly of claim 1, wherein the rigid outer housing of the compact scanning assembly has an outer diameter of 2.4 mm.

7. The endomicroscope assembly of claim 1, wherein the rigid outer housing of the compact scanning assembly has an outer diameter of below 2.4 mm.

8. The endomicroscope assembly of claim 1, further comprising a rigid end tube connector having an outer diameter sized to marry with an inner diameter of the rigid outer housing and an inner diameter of the flexible tubing, the rigid end tube connector positioned to retain the rigid outer housing in engagement with the flexible tubing while allowing rotational movement between the two.

9. The endomicroscope assembly of claim 1, wherein the comb filter drive comprises an inner comb filter drive and an outer comb filter drive each configured to provide electrostatic actuation to rotate the scanning mirror around an X-axis and a Y-axis, respectively, in response to drive signals.

* * * * *